United States Patent
Amend, Jr. et al.

(10) Patent No.: US 9,579,219 B2
(45) Date of Patent: Feb. 28, 2017

(54) ROBOTIC APPARATUS, METHOD, AND APPLICATIONS

(71) Applicant: CORNELL UNIVERSITY, Ithaca, NY (US)

(72) Inventors: John R. Amend, Jr., Ithaca, NY (US); Hod Lipson, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/438,368

(22) PCT Filed: Oct. 25, 2013

(86) PCT No.: PCT/US2013/066803
§ 371 (c)(1),
(2) Date: Apr. 24, 2015

(87) PCT Pub. No.: WO2014/066753
PCT Pub. Date: May 1, 2014

(65) Prior Publication Data
US 2015/0272749 A1    Oct. 1, 2015

Related U.S. Application Data

(60) Provisional application No. 61/718,236, filed on Oct. 25, 2012.

(51) Int. Cl.
*B66C 1/42*  (2006.01)
*A61F 2/58*  (2006.01)
(Continued)

(52) U.S. Cl.
CPC ............. *A61F 2/586* (2013.01); *A61F 2/588* (2013.01); *B25J 15/0023* (2013.01); *B25J 15/08* (2013.01);
(Continued)

(58) Field of Classification Search
CPC .... B25J 15/0009; B25J 15/08; B25J 15/0023; B25J 15/12; B66C 1/422; H01L 21/68707;
(Continued)

(56) References Cited

U.S. PATENT DOCUMENTS 6,505,870 B1 *  1/2003  Laliberte ............... B25J 15/103
                                                     294/106
6,578,893 B2     6/2003  Soucy et al.
(Continued)

FOREIGN PATENT DOCUMENTS

JP       05285877 A      11/1993
WO    2011130475 A2      10/2011

OTHER PUBLICATIONS

International Search Report Form PCT/ISA/220, International Application No. PCT/US2013/066803, pp. 1-3, International Filing Date Oct. 25, 2013.

*Primary Examiner* — Stephen Vu
(74) *Attorney, Agent, or Firm* — William Greener; Bond, Schoeneck & King, PLLC (57) ABSTRACT

A dexterous robotic apparatus includes an asymmetrical hand mechanism including only two finger components: a first independent finger and a second independent finger, and a respective first finger motor and a respective second finger motor disposed in the hand mechanism, wherein the hand mechanism is characterized by only two continuous degrees of freedom.

7 Claims, 4 Drawing Sheets

(51) Int. Cl.
  *B25J 15/08* (2006.01)
  *B25J 15/00* (2006.01)
  *B25J 15/12* (2006.01)
  *A61F 2/54* (2006.01)

(52) U.S. Cl.
  CPC ......... *B25J 15/12* (2013.01); *A61F 2002/543* (2013.01)

(58) Field of Classification Search
  CPC .... H01L 21/67742; A61F 2/586; A61F 2/588; A61F 2002/543
  USPC .................................. 294/86.4, 106, 198
  See application file for complete search history.

(56) References Cited

U.S. PATENT DOCUMENTS

| | | | |
|---|---|---|---|
| 6,817,640 B2 | 11/2004 | Menon et al. | |
| 6,918,622 B2* | 7/2005 | Kim | B25J 15/10 294/106 |
| 7,904,198 B2* | 3/2011 | Hawes | B25J 15/0253 198/459.6 |
| 8,651,543 B2 | 2/2014 | Matsuoka et al. | |
| 2008/0131253 A1 | 6/2008 | Scott et al. | |
| 2011/0148132 A1* | 6/2011 | Park | B25J 15/0266 294/106 |
| 2011/0241369 A1* | 10/2011 | Kamon | B25J 9/102 294/213 |

\* cited by examiner

ROBOTIC APPARATUS, METHOD, AND APPLICATIONS

RELATED APPLICATION DATA

The instant application claims priority to U.S. provisional application Ser. No. 61/718,236 filed Oct. 25, 2012, the subject matter of which is incorporated herein by reference in its entirety.

GOVERNMENT FUNDING

This invention was made with Government support from the National Science Foundation under Project ID Number EFRI 0735953. The United State Government has certain rights in the invention.

BACKGROUND

1. Field of the Invention

Embodiments of the invention are in the field of robotics. More particularly, embodiments of the invention pertain to a dexterous robotic apparatus, associated methods, and applications thereof and, most particularly, to a two-finger, dexterous robotic hand, associated methods, and applications thereof.

2. Related Art

Grasping and dexterous manipulation rank among the principal grand challenges in robotics. Proposed solutions typically involve complex robot hands that take inspiration from the human hand, often with nine or more independent degrees of freedom.

Engineers have endeavored to replicate the human hand since at least 202 BC, at first only aesthetically, and later with increasing functionality. For a good part of this time, efforts were focused only on prosthetic devices, but starting in the late 1960's concurrent advancements in electronics, computers, and robotics opened the door for research into dexterous hands for robots as well. The competence of the human hand is one of the central evolutionary advantages that humans possess, thus restoring this functionality for amputees and furthering these capabilities in robots are important goals.

One of the central challenges for both prosthetic and robot hands is to achieve dexterous manipulation; i.e., the movement of a grasped object within the workspace of the hand. Since robot hands are not subject to the many design constraints of prosthetics (weight, size, power, controllable degrees of freedom) they have served as the primary platform for grasping and dexterous manipulation research. Greater than one hundred different robot hand designs have been proposed by researchers in the last forty years. While great strides have been made in grasping, the achievement of human-level manipulation by robots has remained elusive.

Dexterous manipulation is a task-centric concept, meaning that a hand can be classified as dexterous through the demonstration of certain in-hand manipulations of an object. Enumerating these requisite manipulation tasks is, however, a topic of some uncertainty. The two prevailing metrics for evaluating robotic dexterous manipulation are:

1. Demonstrations from among several basic classes of in-hand movements, most recently separated into six specific classes for robots: regrasping, in-grasp manipulation, finger gaiting, finger pivoting/tracking, rolling, and sliding.

2. Demonstration of a sufficiently broad set of real world manipulation tasks that are typically some combination of those proposed in the Activities of Daily Living (M. P. Lawton, E. M. Brody, Assessment of older people: self-maintaining and instrumental activities of daily living, The Gerontologist 9, 179-186, 1969), Cutkosky's taxonomy of manufacturing grasps (M. R. Cutkosky, On grasp choice, grasp models, and the design of hands for manufacturing tasks, IEEE Transactions on Robotics and Automation 5, 269-279, 1989), the DARPA ARM-H project announcement challenge tasks (DARPA-BAA-10-29, *Autonomous Robotic Manipulation Hardware Track (ARM-H)*, 2010), or other examples contrived to illustrate the capabilities of a particular hand.

In 1984, while describing the famous Utah/MIT dexterous robot hand, Jacobsen et al. (S. C. Jacobsen, J. E. Wood, D. R. Knutti, K. B. Biggers, The Utah/MIT dexterous hand: work in progress, IJRR 3, 21-50, 1984) articulated the viewpoint which had been, and which has remained, the longstanding sentiment of researchers in the field: "The natural manipulation system found in humans is complex. . . . It should be expected that the construction of an artificial counterpart will also include significant complexity." The human hand has 22 degrees of freedom (DOF) and as a result many proposed robot hands have been designed with a similar level of complexity. For those robot hands that do not adhere to anthropomorphism so strictly, designs are typically based on the work of Salisbury (M. T. Mason, J. K. Salisbury Jr., Robot Hands and the Mechanics of Manipulation (The MIT Press, Cambridge, 1985), who found that under certain conditions a minimum of three fingers and nine DOF are needed to satisfactorily perform arbitrary manipulations.

Controlling hands with nine or more DOF can be a difficult task, as evidenced by the large body of work that exists in grasp algorithm research. Some recent work has put forth the view that human-level grasping and manipulation can perhaps be achieved with fewer DOF and fewer actuators by taking advantage of synergies between actuators, and underactuation in mechanical design. Several reported underactuated hands have had success grasping a wide variety of objects with four DOF or fewer, but relatively little progress has been made in the area of dexterous manipulation. Table 1 compares the reported performance of some of the most well known robot hands in order to illuminate the state of the art in robotic dexterous manipulation. Table I compares the reported performance of some of the most well known robot hands in the literature in order to illuminate the state of the art in robotic dexterous manipulation. Among the many robot hands that have been proposed in the literature, the focus of their accompanying publications has often been on the design, manufacturing, and control strategies that are implemented in the given prototype. Relatively few papers present quantitative performance data, and often, terms like dexterous manipulation are used liberally or are simply assumed without explicit demonstration. Furthermore, most all of these robot hands are singular prototypes produced for research purposes and cannot be obtained for further testing. Therefore, in Table I, the columns indicating achieved grasps and manipulations were inferred where possible if they could not be found specifically reported.

TABLE 1

COMPARISON OF ROBOTIC HANDS.

| Hand | Image | No. of Fingers | No. DOF at Joints | No. of Actuators | Grasps achieved | Basic manipulations achieved* | Real-world dexterous manipulation achievements |
|---|---|---|---|---|---|---|---|
| JamHand | | 2 | 2 | 2† | precision and power grasps | 1, 2, 3, 4, 5, 6 | Operating tweezers, depressing a syringe, writing with a pen, opening a lock with a key, cracking an egg, assembling two LEGOs in-hand, using chopsticks |
| BarrettHand (29) | | 3 | 7 | 4 | precision and power grasps | unreported | some manipulation capabilities assumed but not specifically shown |
| DEKA Luke Arm (42-44) | | 5 | unreported | unreported | precision and power grasps | 2 | pouring a grasped measuring cup, operating finger nail clippers, pluking a grape, pouring water, more capabilities assumed |
| DLR Hit Hand II (45) | | 5 | 15 | 15 | human-like grasping assumed | unreported | manipulation capabilities assumed but not specifically shown |
| Gifu Hand (46) | | 5 | 16 | 16 | human-like grasping assumed | unreported | manipulation capabilities assumed but not specifically shown |
| Harada Hand (47) | | 5 | 14 | 5 | precision and power grasps | 2 | operating wire culters, depressing trigger on a grasped hand drill, more capabilities assumed |
| High Speed Hand (48-54) | | 3 | 8 | 5 | precision and power grasps | 1, 2, 5 | knotting a flexible rope, dribbling a ball, spinning a thin rod between fingers, operating tweezers, folding cloth |
| KITECH Hand (55) | | 4 | 16 | 16 | precision and power grasps | 2, 5 | rolling and reorienting various objects |
| Meka H2 Hand (56) | | 4 | 12 | 5 | precision and power grasps | unreported | manipulation capabilities assumed but not specifically shown |
| Robonaut2 Hand (57-59) | | 5 | 12 | 18 | precision and power grasps | unreported | flipping switches, pressing buttons, rotating knobs, handling cloth, operating an air flow meter, operating a hand held drill, operating a portable x-ray device, more capabilities assumed |
| SARAH (32, 60-61) | | 3 | 10 | 2 | precision and power grasps | none demonstrated | no manipulation capabilities demonstrated or assumed |
| Schunk SDH (62) | | 3 | 7 | 7 | precision and power grasps | unreported | some manipulation capabilities assumed but not specifically shown |
| SDM Hand (31, 63-64) | | 4 | 8 | 1 | precision and power grasps | none demonstrated | no manipulation capabilities demonstrated or assumed |
| Shadow Hand (65-67) | | 5 | 20 | 20 or 40‡ | human-like grasping assumed | unreported | manipulation capabilities assumed but not specifically shown |
| SRI Hand (30) | | 4 | 13 | 5§ | precision and power grasps | 1, 2 | turning on a flashlight, more capabilities assumed |
| Stanford/JPL Salisbury Hand (23, 68) | | 3 | 9 | 10 | precision and power grasps | 1, 2, 4, 5 | pivoting, rolling and reorienting grasped objects, more capabilities assumed |
| Utah/MIT Dexterous Hand (21, 69) | | 4 | 16 | 32 | human-like grasping assumed | unreported | manipulation capabilities assumed but not specifically shown |

*inferred where possible: 1) regrasping, 2) in-grasp manipulation, 3) finger gaiting, 4) pivoting, 5) rolling, 6) sliding;
†plus two 3-position values;
‡20 motors or 40 air muscles;
§plus separately controlled brakes at each joint In view of the aforementioned disadvantages, shortcomings, and problems known in the art, the inventors have recognized the benefits and advantages of, as well as the solutions provided by a dexterous robotic hand and associated methods as embodied herein, and dexterous, robotic grasping/gripping/releasing systems incorporating the embodied dexterous robotic hand and associated methods.

SUMMARY

An embodiment of the invention is a dexterous robotic apparatus. The dexterous robotic apparatus includes an asymmetrical hand mechanism including only two finger components: a first independent finger and a second independent finger, and a respective first finger motor and a respective second finger motor disposed in the hand mechanism, wherein the hand mechanism is characterized by only two continuous degrees of freedom (i.e., the two fingers). In various non-limiting, exemplary aspects, the dexterous robotic apparatus may include some or all of the following additional limitations and/or characteristics:

wherein the first independent finger and the second independent finger each have a distal end adapted to receive a gripping and/or jamming apparatus;

wherein the first independent finger and the second independent finger each have a granular material-based jamming/gripper apparatus disposed at the distal end thereof;

further comprising a first finger 3-state valve adapted to evacuate, positively pressurize, or atmospherically neutralize the respective first finger jamming/gripper apparatus and a second finger 3-state valve adapted to evacuate, positively pressurize, or atmospherically neutralize the respective second finger jamming/gripper apparatus;

wherein the first independent finger has a base region and is rotatable about the base region via the first finger motor, and the second independent finger further comprises a linkage mechanism connected to the second finger motor wherein the second independent finger is moveable along a path prescribed by the linkage mechanism;

wherein the linkage mechanism is a four-bar linkage.

An embodiment of the invention is a method for manipulating an object with a dexterous robotic apparatuses described herein.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

FIG. 4(A, B) are Pareto plots showing achievable manipulations vs. robotic hand simplicity, according to a demonstrative aspect of the invention.

DETAILED DESCRIPTION OF EXEMPLARY EMBODIMENTS OF THE INVENTION

In the following description, reference is made to the accompanying drawings that form a part hereof, and in which are shown by way of illustration specific embodiments that may be practiced. These embodiments are described in sufficient detail to enable those skilled in the art to practice the invention, and it is to be understood that other embodiments may be utilized and that structural, logical, and electrical changes may be made without departing from the scope of the present invention. The following description of example embodiments is, therefore, not to be taken in a limited sense.

As used herein, the phrase "universal jamming gripper" means a passive universal gripper as described in E. Brown, N. Rodenberg, J. Amend, A. Mozeika, E. Steltz, M. Zakin, H. Lipson, H. Jaeger, "Universal robotic gripper based on the jamming of granular material," Proc. Natl. Acad. Sci., vol. 107, pp. 18809-18814, November 2010 and as disclosed in International Publication Number WO2011/130475. In summary, a passive universal gripper utilizes an elastic-type membrane (e.g., a balloon) that contains an amount of granular material (e.g., coffee grounds, sand, other). At atmospheric pressure, the granular material is in a fluid-like phase such that it can flow, pour, or even splash. However, when a vacuum is applied, the granular material undergoes a pseudo-jamming-phase transition into a solid-like phase, i.e., there is essentially no relative movement of a single grain with respect to another. When the vacuum is released and the system returns to atmospheric pressure, the granular material will return to the fluid-like phase (either on its own over time or more quickly with external manipulation). This pseudo-phase transition arises out of the inherent solid-liquid duality of granular systems.

All references, including publications, patent applications and patents cited herein are hereby incorporated by reference to the same extent as if each reference were individually and specifically indicated to be incorporated by reference and were set forth in its entirety herein.

The aforementioned universal jamming gripper is not part of the instant invention per se; rather, it illustrates an advantageous mechanism that can be coupled to the disclosed and claimed dexterous robotic apparatus and used to accomplish a variety of grasping and gripping tasks. As such, the enabling description and drawings of the claimed dexterous robotic apparatus include the referenced jamming gripper apparatus merely to facilitate an illustrative understanding of an operative, practical version of the inventive dexterous robotic apparatus.

Figure 1:
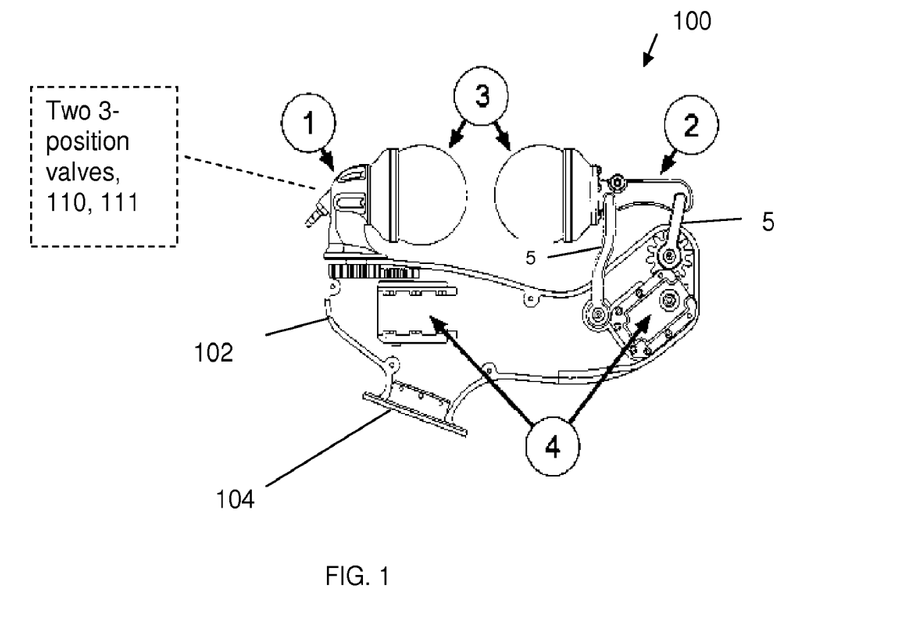
FIG. 1 is a mechanical drawing showing in cross sectional a dexterous robotic apparatus, according to an illustrative embodiment of the invention. The dotted lines represent granular material-based jamming/gripper apparatus disposed at the distal ends of the respective fingers of the dexterous robotic apparatus and are not part of the invention per se.
Figure 2:
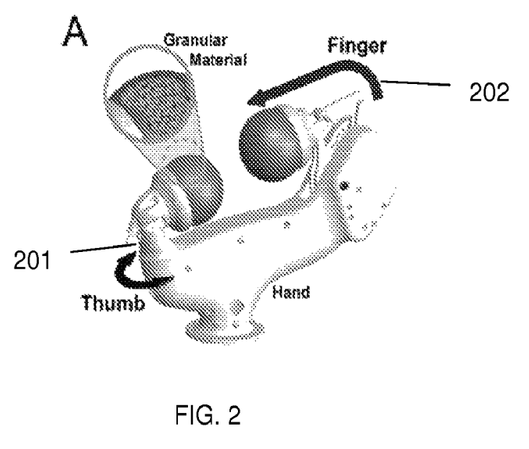
FIG. 2 is a schematic perspective illustration of the illustrative dexterous robotic apparatus of FIG. 1, illustrating the motion parameters of the two fingers.

FIG. 1 shows in cross section, without an outer cover, a dexterous robotic apparatus 100 according to an illustrative embodiment of the invention. The apparatus 100 includes an asymmetrical hand mechanism 102 that is comprised of a base region 104 and a plurality of finger components consisting of a first independent finger, 1, and a second independent finger, 2; and a respective first finger motor, 4A, and a respective second finger motor, 4B, disposed in the hand mechanism 102. The first independent finger 1 has a base region 201 (see FIG. 2) and is rotatable about the base region (see FIG. 2) via the first finger motor 4A. A linkage mechanism 5 is connected to the second finger 2 and to the second finger motor 4B, such that the second independent finger 2 is moveable along a fixed path 202 (see FIG. 2) prescribed by the linkage mechanism. As illustrated, the linkage mechanism 5 is a four-bar linkage. The first independent finger 1 may be considered a 'thumb' and the second independent finger 2 a 'finger' as those terms are used in 'hand' parlance. Together, the two independent fingers represent the only two continuous degrees of freedom in the hand mechanism 102. The finger and the thumb are each driven by a separate servomotor (4A, 4B; e.g., Dynamixel RX-28 servo motors) such that the finger 2 can move along a fixed path 202 (see FIG. 2) prescribed by a 4-bar linkage 5, and the thumb 1 can rotate about its base. It will be appreciated that other driving mechanisms are viable, such as, e.g., pneumatic, hydraulic, electric, etc.). A universal jammer/gripper apparatus 3 is shown coupled to the distal end of each finger. Each of these jammer/gripper fingertips can be controlled by a separate 3-position valve (110, 111) (as described in the references cited herein) so that it can be evacuated, positively pressurized, or neutralized with the atmosphere. These valves are advantageously not contained within the hand mechanism, but rather can be located on a robot arm (not shown) connected to the base region 104 of the hand mechanism 102. Other types of valves or combinations of valves are viable alternatives for the exemplary 3-position valves. It will be appreciated that a variety of alternative gripping, grasping, connecting, pinching, cutting, heating, cooling, electrical, magnetic, or otherwise manipulative or operative 'fingertips' could be coupled to the distal ends of the fingers 1, 2.

Figure 3:
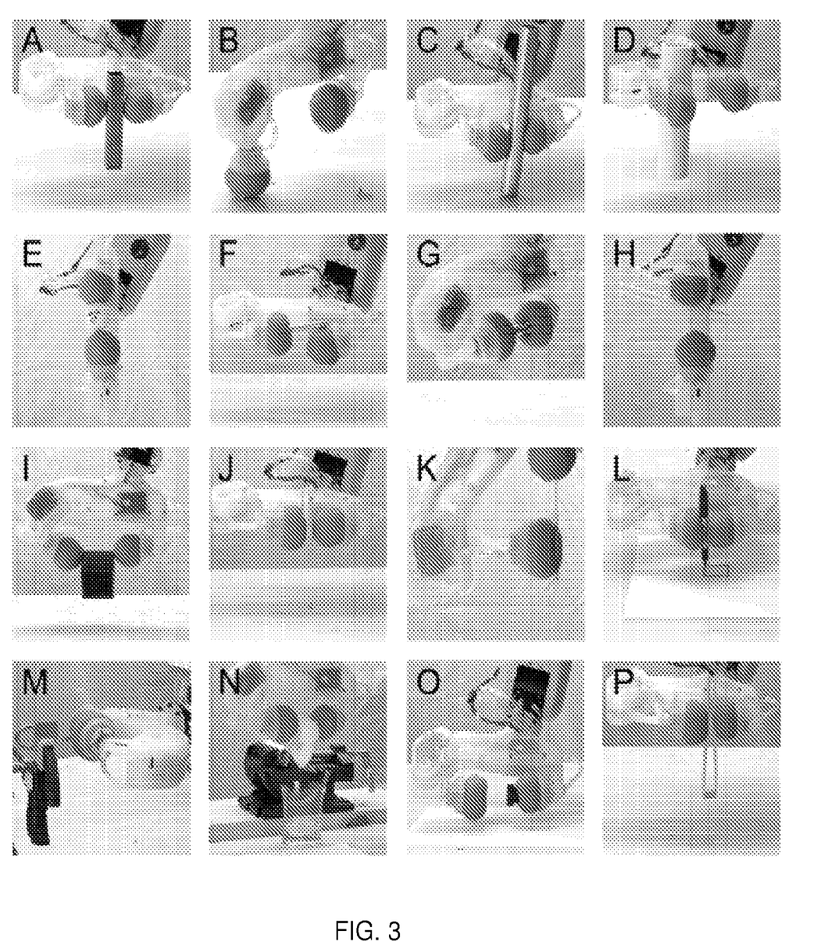
FIG. 3 shows a series of images showing different gripping/grasping capabilities of the illustrative dexterous robotic apparatus of FIG. 1.

For a prototype dexterous robotic apparatus 100, most of the components were 3D printed using an Objet Connex 500 3D printer and Objet's FullCure720 photopolymer material. The 4-bar linkage 5 was printed as one monolithic mechanism and did not require any post-printing assembly. The fingertips each consisted of 250 mL of ground Colombian coffee encased in a latex party balloon. The hand mechanism was driven using Dynamixel RX-28 servo motors. With this prototype, having just two continuous degrees of freedom in the finger joints each driven by a separate servomotor, and two 3-position valves to control the air pressure within the fingertips, the embodied robotic apparatus is able to achieve: multiple precision and power grasps, all six basic dexterous manipulations, and the demonstration of real-world grasping and manipulation tasks. FIG. 3 shows a series of images (A-P) showing different gripping/grasping capabilities of the illustrative, prototype dexterous robotic apparatus including: A) precision grasping, B) a second precision grasp, C) power grasping, D) a second power grasp, E) rolling, F) sliding, G) regrasping, H) finger gaiting, I) pivoting, J) in-hand manipulation, K) operating a syringe, L) writing with a pen, M) opening a lock with a key, N) cracking an egg, O) assembling two LEGOs in-hand, and P) using chop sticks.

Additionally, we have experimentally tested the prototype robotic hand for open loop repeatability of the six basic manipulations, as well as its tolerance for error in the location of the target object. Table II shows the results of these experiments.

TABLE II

RESULTS FROM OPEN LOOP TESTING OF THE JAMHAND'S MANIPULATION REPEATABILITY.

| Manipulation | One time success rate | Maximum repeatability | Error tolerance |
| --- | --- | --- | --- |
| Regrasping | 100% | 8 ± 4 | ±11mm |
| In-grasp manipulation | 84% | >100 | ±9 mm |
| Finger gaiting | 41% | 2 ± 1 | ±0.5 mm |
| Pivoting | 81% | 4 ± 3 | ±2 mm |
| Rolling | 100% | 8 ± 3 | ±4 mm |
| Sliding | 100% | >100 | ±5 mm |

Positive pressure was provided at 620 kPa from a workshop compressed air line, and vacuum was achieved with pump rated for a maximum vacuum of 25 microns. We employed a CRS A465 robot arm for demonstrating and testing the prototype robotic hand. We were able to control the robot arm, valves, and hand motors through a single control program written in C++. In the hand, we achieved a time of 0.5 s for 180° of rotation for the thumb and a time of 0.6 s for the full range of motion of the finger. Maximum pinch force exerted by the fingertips was 80 N.

The second column in Table II reports the one-time repeatability for each manipulation, which is to say if the hand attempts the manipulation, it will succeed at least once on the reported percentage of attempts. The third column in Table II reports the maximum repeatability of a single manipulation, which is to say that if the hand successfully completes the open loop manipulation once, then it can go on to successfully repeat the manipulation the given number of times before failure. The reported range on this value represents the 95% confidence interval.

Error tolerance indicates the ability of the hand to complete the intended manipulation when the target object is located some distance away from its expected pick-up position on the work surface. The distance range for error tolerance reported in Table II indicates the range within which the hand is still able to complete the intended manipulation no less than 95% of the reported value for a one-time manipulation attempt from the second column of Table II; for example, if in open loop the hand can complete the pivoting manipulation at least once on 81% of attempts, then for an error of ±2 mm in any direction on the table, it can still successfully complete the open loop pivoting manipulation at least once on no less than 77% of 270 attempts.

Figure 4:
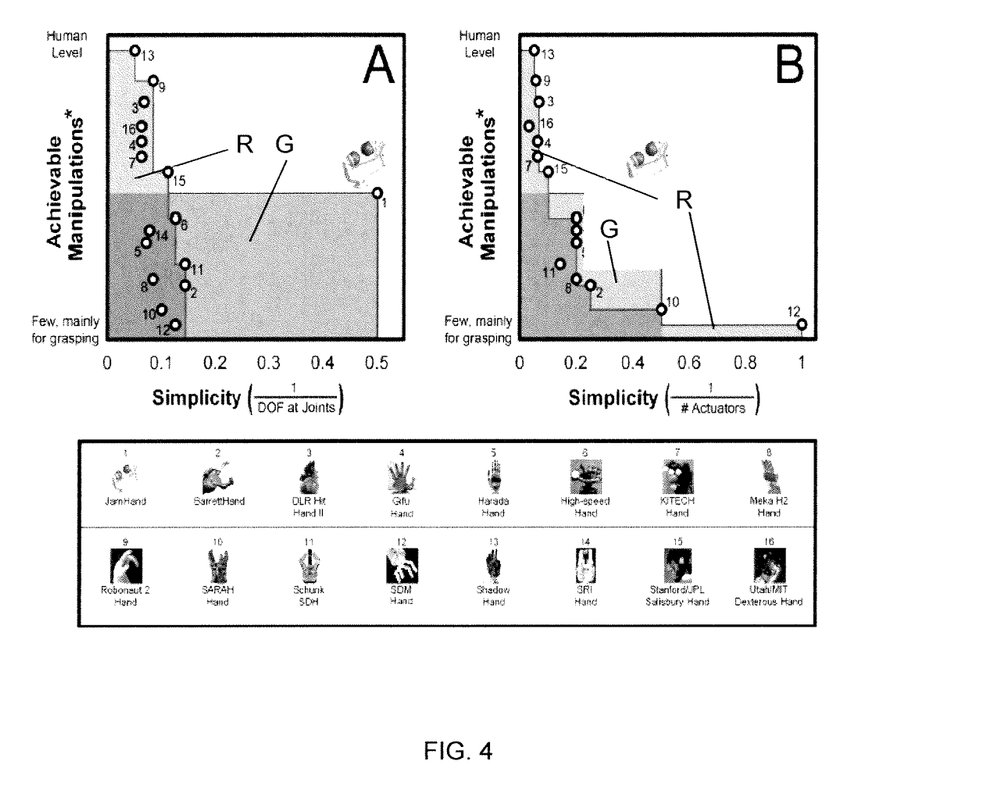

FIG. 4(A, B) shows Pareto plots showing achievable manipulations vs. robotic hand simplicity. Two possible metrics for simplicity are shown: (A) the number of degrees of freedom (DOF) of the hand, and (B) the number of actuators. Both simplicity metrics are divided into one in order to preserve the max-max axis convention of a typical Pareto plot. Both plots show the existing Pareto-dominated region, R, and the new region, G, dominated by the embodied robotic hand. Units on the ordinate axis are arbitrary. Vertical placement of points is based on a qualitative comparison of manipulation capabilities as reported in the literature and aggregated in Table I. Note that quantitative performance evaluations only exist for very few other hands.

FIG. 4 further reveals that the embodied dexterous robotic hand is a clear outlier among state of the art robotic hands for its manipulation capabilities compared to its simplicity. Two metrics for simplicity (DOF and number of actuators) are considered in FIG. 4. Notably absent from FIG. 4 are simpler actuators such as valves and breaks. These devices are sometimes called activators to emphasize their simplicity compared to more traditional actuators. It is clear that a break or valve, which is only capable of on-off operation, is far simpler to control than a motor. However, since no convention exists for directly comparing actuators and activators, activators are not included in FIG. 4.

The embodied dexterous robotic hand represents a significant step forward in the pursuit of dexterous robotic manipulation, and it carves out a broad new region in the performance space of existing robot hands.

We believe that long held assumptions regarding the complexity level necessary in robotic hand design may give way to simpler, lower-cost solutions for achieving human-level grasping and manipulation. With lower complexity devices we can begin to address legacy problems such as the exorbitant cost of multifingered robot hands capable of grasping and dexterous manipulation, as well as limitations in prosthetics, where controlling more than one or two DOFs has been a primary obstacle. It has long been predicted that artificial hands and the tools they use may undergo coevolution to their mutual benefit, much as we have seen with human hands and modern tools. High-functioning non-anthropomorphic designs that are easy to implement are a first step toward achieving this goal.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:
1. A robotic apparatus, comprising:
   an asymmetrical hand mechanism comprising a base region and a plurality of finger components consisting of a first independent finger and a second independent finger; and
   a respective first finger motor and a respective second finger motor disposed in the hand mechanism.
2. The robotic apparatus of claim 1, wherein the first independent finger and the second independent finger each have a distal end adapted to receive a gripping and/or jamming apparatus.
3. The robotic apparatus of claim 2, wherein the first independent finger and the second independent finger each have a granular material-based jamming/gripper apparatus disposed at the distal end thereof.
4. The robotic apparatus of claim 3, further comprising a first finger 3-state valve and a second finger 3-state valve.
5. The robotic apparatus of claim 4, wherein the first finger 3-state valve and the second finger 3-state valve are adapted to evacuate, positively pressurize, or atmospherically neutralize the respective finger jamming/gripper apparatuses.
6. The robotic apparatus of claim 1, wherein the first independent finger has a base region and is rotatable about the base region via the first finger motor, and the second independent finger further comprises a linkage mechanism connected to the second finger motor wherein the second independent finger is moveable along a path prescribed by the linkage mechanism.
7. The robotic apparatus of claim 6, wherein the linkage mechanism is a four-bar linkage.

* * * * *